(12) United States Patent
Namjoshi et al.

(10) Patent No.: US 11,597,890 B2
(45) Date of Patent: Mar. 7, 2023

(54) BASE STOCKS AND OIL COMPOSITIONS CONTAINING THE SAME

(71) Applicant: ExxonMobil Chemical Patents Inc., Baytown, TX (US)

(72) Inventors: Omkar A. Namjoshi, Houston, TX (US); Kyle G. Lewis, Houston, TX (US); Wenning W. Han, Willowbrook, IL (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 4 days.

(21) Appl. No.: 17/279,496

(22) PCT Filed: Sep. 19, 2019

(86) PCT No.: PCT/US2019/051811
§ 371 (c)(1),
(2) Date: Mar. 24, 2021

(87) PCT Pub. No.: WO2020/068527
PCT Pub. Date: Apr. 2, 2020

(65) Prior Publication Data
US 2021/0388282 A1    Dec. 16, 2021

Related U.S. Application Data

(60) Provisional application No. 62/737,152, filed on Sep. 27, 2018.

(51) Int. Cl.
*C10M 107/10* (2006.01)
*C07C 2/22* (2006.01)
(Continued)

(52) U.S. Cl.
CPC ............. *C10M 107/10* (2013.01); *C07C 2/22* (2013.01); *C07C 5/03* (2013.01);
(Continued)

(58) Field of Classification Search
CPC ........ C10M 107/10; C10M 2205/0285; C10N 2020/02; C10N 2030/02; C10N 2030/74;
(Continued)

(56) References Cited

U.S. PATENT DOCUMENTS 4,218,330 A * 8/1980 Shubkin .................... C07C 9/22
508/412
6,824,671 B2 * 11/2004 Goze .................... C10M 107/12
208/19

(Continued)

FOREIGN PATENT DOCUMENTS

JP    2008/094969    4/2008
WO    2003/020856    3/2003
(Continued)

*Primary Examiner* — James C Goloboy
(74) *Attorney, Agent, or Firm* — ExxonMobil Chemical Patents Inc.

(57) ABSTRACT

This disclosure relates to base stocks comprising a C28-C32 hydrocarbon fraction and optionally a C42-C48 hydrocarbon fraction produced by dimerization and trimerization of a linear C14 mono-olefin, a linear C16 mono-olefin, or a mixture thereof, in the presence of a Lewis acid, oil compositions comprising such base stock(s), and processes for making such base stocks.

21 Claims, 4 Drawing Sheets

(51) Int. Cl.
    *C07C 5/03*      (2006.01)
    *C10N 20/02*     (2006.01)
    *C10N 30/02*     (2006.01)
    *C10N 40/25*     (2006.01)
    *C10N 70/00*     (2006.01)
    *C10N 30/00*     (2006.01)

(52) U.S. Cl.
    CPC ............... *C07C 2527/1213* (2013.01); *C10M 2205/0285* (2013.01); *C10N 2020/02* (2013.01); *C10N 2030/02* (2013.01); *C10N 2030/74* (2020.05); *C10N 2040/25* (2013.01); *C10N 2070/00* (2013.01)

(58) Field of Classification Search
    CPC .. C10N 2040/25; C10N 2070/00; C07C 2/22; C07C 5/03; C07C 2527/1213
    See application file for complete search history.

(56)                References Cited

U.S. PATENT DOCUMENTS

| 2007/0293712 | A1  | 12/2007 | Tiitta et al. |
| 2013/0245343 | A1* | 9/2013  | Emett ................. C10M 143/08 585/530 |
| 2017/0211007 | A1  | 7/2017  | Deckman et al. |
| 2019/0062234 | A1* | 2/2019  | Chen ......................... C07C 2/34 |
| 2020/0102519 | A1  | 4/2020  | Oumar-Mahamat et al. |

FOREIGN PATENT DOCUMENTS

| WO | 2017/083086 | 5/2017 |
| WO | 2018/089457 | 5/2018 |

\* cited by examiner

BASE STOCKS AND OIL COMPOSITIONS CONTAINING THE SAME

CROSS-REFERENCE TO RELATED APPLICATIONS

This application is a National Phase Application claiming priority to PCT Application Serial No. PCT/US2019/051811 filed Sep. 19, 2019, which claims priority to the U.S. Provisional Application No. 62/737,152, filed Sep. 27, 2018, the disclosures of which is are incorporated herein by reference.

FIELD OF THE DISCLOSURE

This disclosure relates to base stocks, oil compositions comprising them and processes for making the oil base stocks and the oil compositions. In particular, this disclosure relates to high pour-point oil base stocks suitable for lubricating oil formulations such as engine oil formulations, lubricating oil formulations containing the high pour-point base stocks, and methods for making such base stocks. The base stocks of this disclosure are particularly useful for formulating 0W grades engine oils.

BACKGROUND OF THE DISCLOSURE

Automotive engine oils typically conform to the SAE J300 metric for grading engine oil viscosity. For each SAE engine oil grade (e.g., 0W-4, 0W-8, 0W-12, 5W-10, 5W-20, 10W-30, etc.) there are maximum and minimum viscosity requirements at both high and low temperatures. Typically, such high temperature viscosity requirements are expressed as a permitted range of kinematic viscosity at 100° C. determined pursuant to ASTM D445 ("KV100"), and such low temperature viscosity requirements are expressed as a permitted range of cold cranking simulator viscosity determined pursuant to ASTM D5293 ("CCSV"). For example, the requirements for a 0W grade engine oil include a KV100 of at least 3.8 cSt, and a CCSV at −35° C. no higher than 6,200 mPa·s.

Recently, API Group IV base stocks, which are polyalpha-olefins ("PAO"), have found wide use in high-quality engine oils in various grades, gear box lubricants, and industrial oils. Currently low-viscosity Group IV PAO base stocks having a KV100 in the range from 3 to 10 cSt made from oligomerization of alpha-olefin monomer(s) comprising 8-12 carbon atoms in the presence of a Lewis acid catalyst such as $BF_3$ ("conventional low-viscosity PAO") are commercially available. These conventional low-viscosity PAO base stocks are substantially free of dimers of the monomer(s), and tend to comprise trimers and/or higher oligomers of the alpha-olefin monomer(s) at various concentrations. The trimer and higher oligomer molecules in these base stocks tend to be highly branched (containing more than 2 branches per oligomer molecule on average). While these base stocks provide good performances, to formulate high-quality engine oils for the newer generation engines of modern automobiles, base stocks with even lower viscosity, higher viscosity index, low Noack volatility, and high blending performances in terms of blended CCSV are needed.

This disclosure meets this and other needs.

SUMMARY OF THE DISCLOSURE

In a surprising and counterintuitive manner, it has been found that oligomers of linear mono-olefin(s) comprising 14 or 16 carbon atoms or mixtures thereof made by using conventional Lewis acid catalyst comprising dimers and optionally trimers can be used as high-viscosity-index, low-viscosity base stock suitable for high-quality engine oils, notwithstanding the relatively high pour-points thereof.

A first aspect of this disclosure relates to a base stock comprising a C28-C32 hydrocarbon fraction ("dimers") and optionally a C42-C48 hydrocarbon fraction ("trimers") produced by oligomerization of a linear C14 mono-olefin, a linear C16 mono-olefin, or a mixture thereof, in the presence of a Lewis acid catalyst.

A second aspect of this disclosure relates to a base stock comprising substantially saturated olefin oligomers having the following properties: comprising a C28 to C32 hydrocarbon first fraction at a concentration in the range from 80 to 100 wt %, and a C42 to C48 second fraction at a concentration in the range from 0 to 20 wt %, based on the total weight of the base stock; a kinematic viscosity at 100° C. as determined pursuant to ASTM D445 ("KV100") in the range from 3.3 to 4.6 cSt; a pour point as determined pursuant to ASTM D5850 in the range from −45 to −15° C.; and a cold-crank-simulator viscosity as determined pursuant to ASTM D5293 ("CCSV") at −35° C. of at least 500 mPa·s.

A third aspect of this disclosure relates to an oil composition comprising a base stock of the first aspect or the second aspect as a first base stock, and optionally a Group II, III, IV, or V base stock different from the first base stock as a second base stock.

A fourth aspect of this disclosure relates to a process for making a base stock, the process comprising: (I) providing an olefin monomer feed comprising a C14 linear mono-olefin, a C16 linear mono-olefin, or a mixture thereof; (II) contacting the olefin monomer(s) with a catalyst system comprising a Lewis acid in at least one oligomerization reactor under oligomerization conditions to obtain an oligomerization reaction mixture comprising unreacted olefin monomer, dimers, trimers, and the catalyst system; (III) quenching the oligomerization reaction mixture; (IV) removing the unreacted monomer(s) from the quenched oligomerization reaction mixture after step (III) to obtain an unsaturated product precursor; and (V) optionally hydrogenating the unsaturated product precursor in a hydrogenation reactor in the presence of hydrogen under hydrogenation conditions to obtain a hydrogenated oligomer oil; and (VI) obtaining the base stock comprising the dimers and optionally the trimers from the unhydrogenated product precursor or hydrogenated dimers and optionally hydrogenated trimers from the hydrogenated oligomer oil.

Further objects, features and advantages of this disclosure will be understood by reference to the following drawings and detailed description.

DETAILED DESCRIPTION OF THE DISCLOSURE

Definitions

Figure 1:
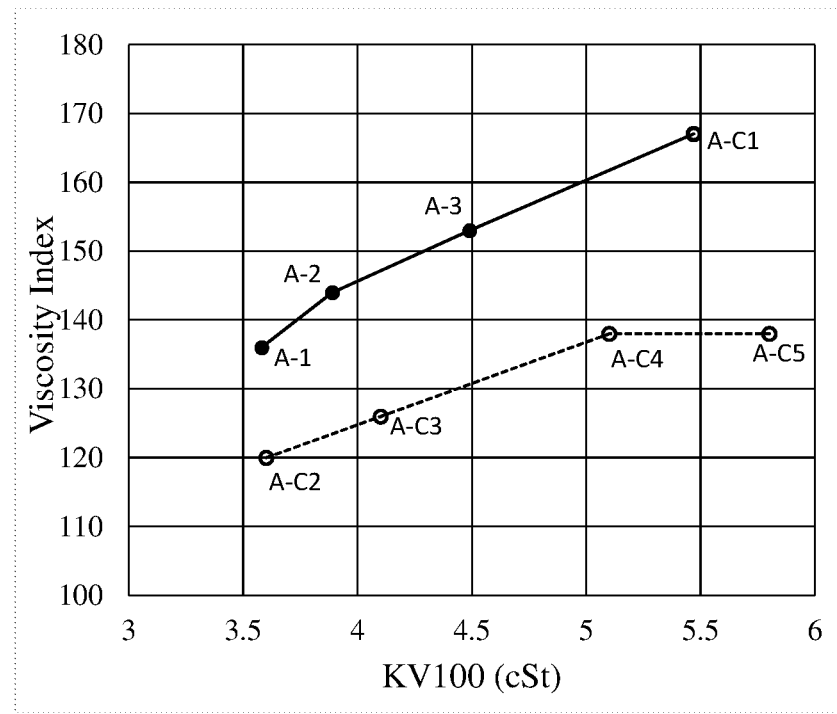
FIG. 1 is a chart showing the viscosity index as a function of kinematic viscosity at 100° C. of the base stocks of the inventive and comparative examples in Part A of the Examples in this disclosure.

"Alkyl group" refers to a saturated hydrocarbyl group consisting of carbon and hydrogen atoms.

"Hydrocarbyl group" refers to a group consisting of hydrogen and carbon atoms only. A hydrocarbyl group can be saturated or unsaturated, linear or branched, cyclic or acyclic, and aromatic or non-aromatic.

"Hydrocarbon" refers to a compound consisting of carbon atoms and hydrogen atoms.

"Alkane" refers to a hydrocarbon that is completely saturated. An alkane can be linear, branched, cyclic, or substituted cyclic.

"Olefin" refers to a non-aromatic hydrocarbon comprising one or more carbon-carbon double bond in the molecular structure thereof.

"Mono-olefin" refers to an olefin comprising a single carbon-carbon double bond.

"Cn" group or compound refers to a group or a compound comprising carbon atoms at total number thereof of n. Thus, "Cm-Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

"Carbon backbone" refers to the longest straight carbon chain in the molecule of the compound or the group in question. "Branch" refer to any substituted or unsubstituted hydrocarbyl group connected to the carbon backbone. A carbon atom on the carbon backbone connected to a branch is called a "branched carbon."

"Epsilon-carbon" in a branched alkane refers to a carbon atom in its carbon backbone that is (i) connected to two hydrogen atoms and two carbon atoms and (ii) connected to a branched carbon via at least four (4) methylene ($CH_2$) groups. Quantity of epsilon carbon atoms in terms of mole percentage thereof in a alkane material based on the total moles of carbon atoms can be determined by using, e.g., $^{13}C$ NMR.

"SAE" refers to SAE International, formerly known as Society of Automotive Engineers, which is a professional organization that sets standards for internal combustion engine lubricating oils.

"SAE J300" refers to the viscosity grade classification system of engine lubricating oils established by SAE, which defines the limits of the classifications in rheological terms only.

"Base stock" or "base oil" interchangeably refers to an oil that can be used as a component of lubricating oils, heat transfer oils, hydraulic oils, grease products, and the like.

"Lubricating oil" or "lubricant" interchangeably refers to a substance that can be introduced between two or more surfaces to reduce the level of friction between two adjacent surfaces moving relative to each other. A lubricant base stock is a material, typically a fluid at various levels of viscosity at the operating temperature of the lubricant, used to formulate a lubricant by admixing with other components. Non-limiting examples of base stocks suitable in lubricants include API Group I, Group II, Group III, Group IV, and Group V base stocks. PAOs, particularly hydrogenated PAOs, have recently found wide use in lubricants as a Group IV base stock, and are particularly preferred. If one base stock is designated as a primary base stock in the lubricant, additional base stocks may be called a co-base stock.

"In the vicinity of" a given temperature means within the range from 10° C. lower than that temperature to 10° C. higher than that temperature.

"Substantially saturated" means at least 90%, preferably at least 95%, more preferably at least 98%, by mole, of the molecules in question are saturated, based on the total moles of the relevant molecules.

"Substantially free" of the monomer(s) means a material comprises the monomer(s) at a total concentration thereof, of no more than 5%, preferably no more than 3%, more preferably no more than 1%, by weight, based on the total weight of the material.

All kinematic viscosity values in this disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in this disclosure are as determined pursuant to ASTM D2270.

All Noack volatility ("NV") values in this disclosure are as determined pursuant to ASTM D5800 unless specified otherwise. Unit of all NV values is wt %, unless otherwise specified.

All pour point values in this disclosure are as determined pursuant to ASTM D5950 or D97.

All CCS viscosity ("CCSV") values in this disclosure are as determined pursuant to ASTM 5293. Unit of all CCSV values herein is millipascal second (mPa·s, which is equivalent to centipoise), unless specified otherwise. All CCSV values are measured at a temperature of interest to the lubricating oil formulation or oil composition in question. Thus, for the purpose of designing and fabricating engine oil formulations, the temperature of interest is the temperature at which the SAE J300 imposes a minimal CCSV.

All percentages in describing chemical compositions herein are by weight unless specified otherwise. "Wt %" means percent by weight.

All numerical values within the detailed description and the claims herein are modified by "about" or "approxi-

I. The Base Stock of this Disclosure

I.1 General

This disclosure first relates to a base stock comprising a C28-C32 hydrocarbon fraction ("dimers") and optionally a C42-C48 hydrocarbon fraction ("trimers") produced by dimerization and trimerization of a linear C14 mono-olefin, a linear C16 mono-olefin, or a mixture thereof, as the monomer in the presence of a Lewis acid catalyst such as $BF_3$. The base stock of this disclosure can be substantially unsaturated or substantially saturated. Preferably, the base stock of this disclosure is substantially saturated, especially if it is intended for use in lubricating oil compositions, heat transfer oils, and hydraulic oils desired to have a long service life. If unsaturated, at least some of the dimer and/or trimer molecules comprise a carbon-carbon double bond, which are highly reactive and can cause instability to the base stock during use. The reactivity of such carbon-carbon double bonds can make such unsaturated base stock useful as intermediates for making other chemical materials by reacting with functionalizing agents to produce, among others, functionalized dimers and/or trimers.

The base stock of this disclosure can be advantageously substantially free of the C14 and/or C16 monomer(s) and the hydrogenated alkanes thereof. Such monomers and hydrogenated alkanes thereof, if present in the base stock at high quantity, can cause the base stock to have a high Noack volatility, which is highly undesirable.

The dimer molecules in the base stock of this disclosure are typically branched hydrocarbons, preferably branched alkanes, having a long carbon backbone. Thus, for the dimer molecules derived from two C14 mono-olefin molecules, the long carbon backbone can comprise, e.g., 20, 21, 22, 23, 24, 24, 25, 26, or 27 carbon atoms. For dimer molecules derived from two C16 mono-olefin molecules, the long carbon backbone can comprise, e.g., 24, 25, 26, 27, 28, 29, 30, or 31 carbon atoms. For dimer molecules derived from one C14 mono-olefin molecule and one C16 mono-olefin molecule, the long carbon backbone can comprise, e.g., 22, 23, 24, 25, 26, 27, 28, or 29 carbon atoms. The dimer molecules can comprise one or more branches connected to the carbon backbone. The dimer molecules of the base stock of this disclosure comprise, on average per molecule, more than one (1) branches connected to the carbon backbone. Preferably, the dimer molecules of the base stock of this disclosure comprise, on average per molecule, less than two (2) branches connected to the carbon backbone. Preferably, the dimer molecule of the base stock of this disclosure comprises, on average per molecule, from 1.1 to 1.9 branches, 1.2 to 1.8 branches, 1.3 to 1.7 branches, 1.4 to 1.6 branches, or 1.5 to 1.6 branches. Average number of branches in an alkane material can be determined using $^{13}C$ NMR. Compared to the dimer molecule of 1-tetradecene made by coordination insertion oligomerization using a metallocene catalyst, the dimer molecules in the base stock of this disclosure tend to have significantly higher number of branches on average per molecule. Without intending to be bound by a particular theory, it is believed this is due to the use of Lewis acid catalyst such as $BF_3$ in the process of making the material, which simultaneously catalyzes the oligomerization reactions between the monomer molecules, the isomerization of the monomer molecules and other reactions, leading to multiple branches with various length in the dimer molecules. On the other hand, compared to the trimer molecules of 1-decene made by oligomerization catalyzed by similar Lewis-acid catalyst such as $BF_3$, the dimer molecules in the base stock of this disclosure tend to have significantly higher linearity characterized by a longer carbon backbone and much fewer branches connected to the carbon backbone. The significantly higher linearity renders the dimer molecules in the base stock of this disclosure significantly waxier than the 1-decene trimer molecules, which is believed to cause many surprising, interesting and advantageous lubricant properties of the base stocks of this disclosure, as the Examples section of this disclosure clearly demonstrates.

The trimer molecules in the base stock of this disclosure are branched hydrocarbons, preferably branched alkanes. Because they are produced from the oligomerization of three monomer molecules, they tend to have, on average per molecule, higher number of branches connected to the carbon backbone therein than the dimers. It is believed that the trimers in the base stock of this disclosure resembles the molecular structures of the trimers made from C8-C12 linear alpha-olefins in conventional low-viscosity base stocks commercially available discussed above.

The base stock of this disclosure preferably comprises predominantly dimers. Thus, the base stock of this disclosure can comprise the dimers at a concentration in the range from c1 to c2 wt %, based on the total weight of the base stock, where c1 and c2 can be, independently: 80, 81, 82, 83, 84, 85, 86, 87, 88, 89, 90, 91, 92, 93, 94, 95, 96, 97, 98, 99, or 100, as long as c1<c2. Preferably c1=80 and c2=100; more preferably c1=82 and c2=99; still more preferably c1=85 and c2=98, still more preferably c1=86 and c2=96, still more preferably c1=88 and c2=95, and still more preferably c1=90 and c2=94. For the base stocks made from the same monomer composition, the higher the concentration of the dimers, the lower the KV100 of the base stock tends to be.

The base stock of this disclosure, including but not limited to those having the feature(s) described above, can preferably comprise the trimers as a minor component. Thus, the base stock of this disclosure can comprise the trimers at a concentration in the range from c3 to c4 wt %, based on the total weight of the base stock, where c3 and c4 can be, independently: 0, 1, 2, 3, 4, 5, 6, 7, 8, 9, 10, 11, 12, 13, 14, 15, 16, 17, 18, 19, or 20, as long as c3<c4. Preferably c3=0 and c4=20; more preferably c3=2 and c4=18; still more preferably c3=4 and c4=16, still more preferably c3=5 and c4=85, still more preferably c3=5 and c4=86; still more preferably c3=5 and c4=88; and still more preferably c3=5 and c4=90. For the base stocks made from the same monomer composition, the higher the concentration of the trimers, the higher the KV100 of the base stock tends to be. A high concentration of dimers in the base stock of this disclosure imparts very interesting lubricant properties to the base stocks of this disclosure surprisingly suitable for formulating high-quality low-viscosity engine oils, especially those in the 0W grade.

The base stock of this disclosure, including but not limited to those having the feature(s) described above, can preferably comprise the dimers and trimers combined at a total concentration thereof of at least 95 wt %, or at least 96 wt %, or at least 97 wt %, or at least 98 wt %, or at least 99 wt %, or at least 99.5 wt %, or at least even 99.9 wt %, based on the total weight of the base stock.

The base stock of this disclosure, including but not limited to those having the feature(s) described above, preferably comprises a C56-C64 hydrocarbon fraction ("tetramers") and hydrocarbon fractions with even larger number of carbon atoms in molecules thereof, if any at all, at a total concentration thereof no higher than 5 wt %, preferably no higher than 4 wt %, more preferably no higher than 3 wt %, still more preferably no higher than 2 wt %, still more preferably no higher than 1 wt %, still more preferably no higher than 0.8 wt %, still more preferably no higher than 0.5 wt %, still more preferably no higher than 0.1 wt %, based on the total weight of the base stock. A high concentration of the tetramers can lead to a high kinematic viscosity at 100° C. of the base stock, which can be undesirable for formulating low-viscosity lubricants.

The base stock of this disclosure, including but not limited to those having the feature(s) described above, can desirably exhibit a pour point determined pursuant to ASTM D5950 in the range from −45 to −10° C., preferably in the range from −40 to −15° C., more preferably from −40 to −20° C., still more preferably from −40 to −25° C., still more preferably from −40 to −30° C., still more preferably from −40 to −35° C. Compared to other low-viscosity Group IV base stocks made from C8-C12 linear alpha-olefin monomer(s) by Lewis-acid catalyzed oligomerization reactions ("conventional low-viscosity PAO base stocks") having similar kinematic viscosity at 100° C., the base stocks of this disclosure exhibit significantly higher pour points, as demonstrated by the examples section of this disclosure. However, surprisingly, the high pour points of the base stocks of this disclosure do not prevent them from blending successfully with conventional PAO base stocks to form high-quality, low-viscosity engine oils.

The base stocks of this disclosure, including but not limited to those having the feature(s) described above, can desirably exhibit a kinematic viscosity at 100° C. determined pursuant to ASTM D445 in the range from 3.0 to 5.0 cSt, preferably from 3.2 to 4.8 cSt, more preferably from 3.3 to 4.5 cSt, still more preferably from 3.4 to 4.2 cSt, and still more preferably from 3.5 to 4.0 cSt. The low KV100 of these base stocks of this disclosure render them particularly suitable as candidate for primary base stock and/or co-base stocks useful for engine oils and other lubricants requiring a low KV100 for the formulation.

The base stocks of this disclosure, including but not limited to those having the feature(s) described above, can desirably exhibit a high viscosity index in the range from 120 to 170, preferably from 125 to 165, more preferably from 130 to 160, still more preferably from 135 to 155. As shown in the Examples section of this disclosure, compared to conventional low-viscosity PAO base stocks, the base stocks of this disclosure tend to have significantly higher viscosity index, which is highly desirable for engine oils and other lubricant products, as well as heat transfer oils and hydraulic oils.

The base stocks of this disclosure, including but not limited to those having the feature(s) described above, can desirably exhibit a Noack volatility determined pursuant to ASTM D5800 no higher than 20 wt %, preferably no higher than 18 wt %, more preferably no higher than 17 wt %, and still more preferably no higher than 15 wt %.

The base stocks of this disclosure, including but not limited to those having the feature(s) described above, can desirably exhibit the following properties when blended with a conventional polyalphaolefin base stock made from C8-C12 linear alphaolefin feed by Lewis acid catalysis having a KV100 of about 4.0 cSt (e.g., in the range from 4.0 to 4.2 cSt), a pour point at most −50° C. (preferably at most −60° C., still more preferably at most −65° C.) ("PAO reference base stock"), to form a first mixture oil comprising the base stock based on the total weight of the first mixture oil, a second mixture oil comprising 20 wt % of the base stock based on the total weight of the second mixture oil, and a third mixture oil comprising 30 wt % of the base stock based on the total weight of the base stock, at least one of the following is met: (i) the first mixture oil exhibits a lower CCSV at −35° C. than the PAO reference base stock; (ii) the second mixture oil exhibits a lower CCSV at −35° C. than the PAO reference base stock; and (iii) the third mixture oil exhibits a lower CCSV at −35° C. than the PAO reference base stock. Preferably at least one of the following is met: (i) the first mixture oil exhibits a CCSV at −35° C. at least 50 mPa·s lower than that of the PAO reference base stock; (ii) the second mixture oil exhibits a CCSV at −35° C. at least 50 mPa·s lower than that of the PAO reference base stock; and (iii) the third mixture oil exhibits a CCSV at −35° C. at least 50 mPa·s lower than that of the PAO reference base stock. Preferably, the base stock exhibits a CCSV at −35° C. higher than that of the PAO reference base stock. In certain embodiments, the base stock preferably exhibits a CCSV at −35° C. higher than 2000 mPa·s. Even though the base stock in neat form exhibits such a high CCSV at −35° C., its binary mixtures with the PAO reference base stock nonetheless can exhibit a CCSV at −35° C. lower than that of the PAO reference base stock and that of the base stock itself. This interesting CCSV behavior of the base stock of this disclosure is very surprising. In other embodiments, the base stock of this disclosure can exhibit a CCSV at −35° C. of lower than 1000 mPa·s (e.g., a base stock comprising at least 90 wt % of dimers of C14 linear alpha-olefins), such low CCSV at −35° C. of such base stock of this disclosure is conducive to a CCSV at −35° C. of the mixtures comprising it and the PAO reference base stock. The CCSV-lowering behavior of the base stock of this disclosure can be observed as well when mixed with conventional low-viscosity PAO base stocks with other viscosities, such as about 5, 6, 7, 8, 9, or 10 cSt, or even with Group II and III base stocks. The CCSV-lowering behavior of the base stock of this disclosure when combined with conventional low-viscosity PAO base stocks and Group II or III base stocks renders it particularly advantageous in formulating engine oils in the 0W grade and other winter grades as a co-base stock with a primary conventional low-viscosity PAO base stock or Group II or III base stock.

II. Method for Making the Base Stock of this Disclosure

The base stock of this disclosure is made by oligomerization of a C14 linear mono-olefin, a C16 linear mono-olefin, or a mixture of a C14 and C16 linear mono-olefin in the presence of a catalyst system comprising a Lewis acid such as $BF_3$ or $AlCl_3$. The process preferably comprises the following steps: (I) providing an olefin monomer feed comprising a C14 linear mono-olefin, a C16 linear mono-olefin, or a mixture thereof; (II) contacting the olefin monomer(s) with a catalyst system comprising a Lewis acid in at least one oligomerization reactor under oligomerization conditions to obtain an oligomerization reaction mixture comprising unreacted olefin monomer(s), dimers, trimers, and the catalyst system; (III) quenching the oligomerization reaction mixture; (IV) removing the unreacted monomer(s) from the quenched oligomerization reaction mixture after step (III) to obtain an unsaturated product precursor; and (V) optionally hydrogenating the unsaturated product precursor in a hydrogenation reactor in the presence of hydrogen under hydrogenation conditions to obtain a hydrogenated oligomer oil; and (VI) obtaining the base stock comprising dimers and optionally trimers from the unhydrogenated product precursor or hydrogenated dimers and optionally hydrogenated trimers from the hydrogenated oligomer oil. In an alternative process, step (V) of hydrogenating the unsaturated product precursor is omitted, and the base stock comprising unsaturated dimers and unsaturated trimers can be obtained directly from the unsaturated product precursor. In one specific embodiment, the unsaturated product precursor comprising the unsaturated dimers and trimers can be used as the base stock of this disclosure as is. Preferably the process for making the base stock of this disclosure includes steps (V) and (VI) above, and the thus-produced base stock comprises saturated dimers and trimers.

The C14 linear mono-olefin can be 1-tetradecene, 2-tetradecene, 3-tetradecene, 4-tetradecene, 5-tetradecene, or 6-tetradecene, or any mixture of two or more thereof, preferably 1-tetradecene. 1-tetradecene is an alpha-olefin; and the rest internal mono-olefins. Commercially available 1-tetradecene typically contain some internal C14 mono-olefins above as impurities. In the oligomerization step (II) above, in the presence of a strong Lewis acid such as $BF_3$, 1-tetradecene may isomerize to form one or more of the internal olefins at various concentrations thereof, which can undergo dimerization and/or trimerization reactions with each other and other mono-olefin monomers to form the oligomerization reaction mixture comprising the monomers and isomers thereof, dimers, trimers, and higher oligomers.

The C16 linear mono-olefin can be 1-hexadecene, 2-hexadecene, 3-hexadecene, 4-hexadecene, 5-hexadecene, 6-hexadecene, or 7-hexadecene, or any mixture of two or more thereof, preferably 1-hexadecene. While 1-hexadecene is an alpha-olefin, the rest are internal mono-olefins. Commercially available 1-hexadecene typically contain some internal C16 mono-olefins above as impurities. In the oligomerization step (II) above, in the presence of a strong Lewis acid such as $BF_3$, 1-hexadecene may isomerize to form one or more of the internal olefins at various concentrations thereof, which can undergo dimerization and/or trimerization reactions with each other and other mono-olefin monomers to form the oligomerization reaction mixture comprising the monomers and isomers thereof, dimers, trimers, and higher oligomers.

The oligomerization reactor in step (II) can be a batch reactor, a semibatch reactor, or a continuous reactor, but preferably a continuous reactor such as a continuously stirred tank reactor ("CSTR"). The reactor can include a single vessel, multiple vessels arranged in parallel, or multiple vessels arranged in series. In a preferred embodiment, in step (II) the reactor is a continuous reactor including two reaction vessels connected in series, wherein the monomers are all charged into the upstream vessel where oligomerization reactions proceed for a first residence time, and the effluent from the upstream vessel is fed into the downstream vessel where oligomerization reactions proceed for a second residence time to produce the oligomerization reaction mixture discharged from the second vessel.

The catalyst system used in the reactor in step (II) includes a Lewis acid such as $BF_3$ and $AlCl_3$, with $BF_3$ preferred. Where $BF_3$ is used, the catalyst system typically further includes a promoter system including an alcohol and optionally an ester. Such alcohol useful in the promoter system include examples such as ethanol, n-propanol, n-butanol, n-pentanol, and the like. Such ester useful in the promoter system include examples such as ethyl acetate, n-butyl acetate, and the like. Many of the alcohols and esters and combinations thereof described in U.S. Pat. No. 7,544,850 can be used in the oligomerization step (II) of the process of this disclosure. Among these, the combination of ethanol and ethyl acetate was found to be most preferred for making a base stock of this disclosure comprising dimers as a predominant component (e.g., comprising dimers at a concentration at least 80 wt % based on the total weight of the base stock) in that it results in a high conversion of the C14 and C16 monomer(s) in the reaction, and a high selectivity toward dimers over trimers and higher oligomers. When ethanol/ethyl acetate combination is used as the promoter for $BF_3$, one can achieve the production of a base stock comprising predominantly dimers without having to separate the dimers from higher oligomers in a distillation step after the removal of monomers in step (IV). When other promoter systems, e.g., butanol/butyl acetate, are used, the selectivity toward trimers and higher oligomers such as tetramers tend to be much higher than when ethanol/ethyl acetate is used, sometimes necessitating a step of separating the dimers from such higher oligomers by distillation after step (IV) in order to produce a base stock comprising dimers as a predominant component.

When a catalyst system comprising $BF_3$, ethanol and ethyl acetate is used, preferably the molar ratio of the monomer feed to $BF_3$ is in the range from 2 to 20, more preferably from 2.5 to 13.5, still more preferably from 3.4 to 10.1, still more preferably from 4 to 10.1, still more preferably from 4.5 to 9 and still more preferably from 5 to 8. Preferably the reaction vessel(s) houses an atmosphere comprising $BF_3$ gas at an absolute partial pressure thereof in a range from 3.4 to 170 kilopascal ("kPa"), more preferably from 14 to 100 kPa, still more preferably from 27 to 69 kPa, and still more preferably from 31 to 37 kPa. Preferably the molar ratio of $BF_3$ to ethanol is in the range from 0.5 to 2.0, more preferably from 0.7 to 2.0, still more preferably from 1 to 2.0, still more preferably from 1.75 to 2.0, and still more preferably from 1.9 to 2.0. Preferably the molar ratio of ethanol to ethyl acetate is in the range from 1 to 3, more preferably from 1 to 2, still more preferably from 1 to 1.5, still more preferably from 1 to 1.25, still more preferably about 1. Where the oligomerization reactor comprises two reaction vessels in series, preferably both vessels house atmosphere having substantially the same partial pressure of $BF_3$, and fresh alcohol and ester, if any, are supplied only to the upstream vessel and carried forward to the second vessel. Such two-reactor arrangement is particularly advantageous in that it promotes a high selectivity toward dimers and a high overall conversion of the monomers in the oligomerization reactions.

The preferred total residence time of the olefin monomer feed in the oligomerization reactor can range from 1 to 20 hours, more preferably from 1.5 to 15 hours, still more preferably from 2 to 12.5 hours, still more preferably from 3 to 10 hours, and still more preferably from 4 to 9 hours. Where two reaction vessels are included in the oligomerization reactor, the residence time in the upstream and downstream vessels can be the same or different. The preferred ratio of residence time in the upstream reaction vessel to the residence time in the downstream reaction vessel can be in the range from 5 to 1 more preferably from 4 to 1 still more preferably from 3 to 1.

The reaction temperature in the oligomerization reactor can be preferably in the range from 10 to 100° C., more preferably from 20 to 80° C., still more preferably from 35 to 65° C., still more preferably from 40 to 60° C., still more preferably from 45 to 55° C. Where the oligomerization reactor comprises two reaction vessels in series, the reaction temperatures in the two vessels can be both in the above ranges and can be the same or different.

As described above, on contact with $BF_3$, a strong Lewis acid, the monomer olefin molecule(s) in the olefin monomer feed can undergo isomerization reactions to produce other olefins, particularly internal olefins if the feed is a linear alpha olefin. The olefin monomer molecules can react with each other and their isomers to produce dimer molecules with various carbon backbones having various branches. Compared to dimers made from linear alpha-olefin molecules in the presence of a coordination insertion polymerization catalyst such as a metallocene catalyst system, the dimers produced in the process of this disclosure tend to have more branches connected to the carbon backbone. Thus, the dimer molecules produced in the process of this disclosure comprise, on average per dimer molecule, more than one (1) branches connected to the carbon backbone. Some of the dimer molecules may comprise only one (1) branch connected to the carbon backbone, some comprise two (2), and a fraction may comprise more than two (2). Nonetheless, preferably, the dimer molecules produced in the oligomerization reactor comprise, on average per molecule, at most 2 branches connected to the carbon backbone. The relatively low branching and the relatively long carbon backbones of the dimer molecules result in relatively high linearity of the molecules, and a relatively high waxiness and relatively high pour point to a base stock of this disclosure comprising predominantly dimers, as discussed above.

The dimer molecules as produced in the oligomerization reactor are mono-olefins per se comprising a carbon-carbon double bond. In the presence of $BF_3$, the dimer molecules can isomerize to form terminal or internal olefins. Some of the dimer molecules or isomers thereof may further react with one additional monomer molecule to form trimer molecules. Some of the dimer molecules or isomers thereof may react with each other to form tetramer molecules. The trimer molecules may react with one additional monomer molecule to form tetramers. Higher oligomers than tetramers can be formed as well. On average, the higher the degree of polymerization required for producing an oligomer, the higher the number of branches connected to the carbon backbone of the oligomer molecule. Thus, on average, tetramers comprise higher number of branches connected to their carbon backbones than trimers, which, in turn, comprise higher number of branches connected to their backbones than dimers. The higher branching of trimers than dimers leads to less linearity of the trimer molecules than the dimer molecules, hence less waxiness thereof.

The oligomerization reaction mixture exiting or taken out of the oligomerization reactor is a mixture comprising unreacted olefin monomer(s), isomers of the olefin monomer(s), dimers of the olefin monomer(s), trimers of the olefin monomer(s), and higher oligomers such as tetramers, and the catalyst system comprising $BF_3$ and the promoter(s). The oligomerization reaction mixture can be quenched by adding an excessive quantity of the promoter, or an alkaline aqueous solution such as NaOH aqueous solution, to deactivate the $BF_3$ catalyst.

The quenched oligomerization reaction mixture can then be distilled to remove the unreacted monomer(s) and isomers thereof and the residual alcohol/ester promoters to yield an unsaturated product precursor. While the unsaturated product precursor can be used as a base stock per se given its lubricant properties, it is preferred that the unsaturated product precursor is hydrogenated in a hydrogenation reactor in the presence of hydrogen under hydrogenation conditions to obtain a hydrogenated oligomer oil that is substantially completely saturated, i.e., substantially all of carbon-carbon double bonds in the oligomer molecules have been hydrogenated. Such hydrogenation conditions can include the presence of a hydrogenation catalyst comprising metals such as Fe, Co, Ni, Re, Pd, Pt, Rh, Ru, and the like.

A preferred hydrogenation catalyst is Raney nickel. Filtration of the catalyst particles from the hydrogenation reaction mixture exiting the hydrogenation reactor yields a hydrogenated oligomer oil. The hydrogenated oligomer oil, comprising saturated dimers and optionally trimers and higher oligomers, can be used directly as a base stock. Alternatively, the hydrogenated oligomer oil may be further separated by distillation to obtain fractions rich in dimers, trimers, or higher oligomers, which can be used as base stocks of various viscosity grades.

III. The Oil Composition Containing the Base Stock of this Disclosure

The base stocks of this disclosure are useful in formulating lubricating oils. In this disclosure, a "lubricating oil formulation" refers to lubricating oil product that can be directly used to lubricate the interface between two surfaces moving relative to each other without the need to add any additional material. An oil composition in this disclosure can be, among others: (i) a pure base stock of this disclosure described above; (ii) a mixture of a base stock of this disclosure described above as a first base stock and at least one additional base stock as a second base stock; (iii) a mixture of a base stock of this disclosure as the first base stock with all other base stocks of a lubricating oil formulation but absent one or more additives in the lubricating oil formulation; (iv) a mixture of a base stock of this disclosure as a first base stock and one or more additives in a lubricating oil formulation but absent one or more additional base stocks in the lubricating oil formulation; or (v) a lubricating oil formulation comprising a base stock as a first base stock, one or more additives, and optionally one or more additional base stocks.

Therefore, to make a final lubricating oil formulation of a product, one may add additional components, such as other base stocks, additional quantities of the materials already present in the oil composition, additive components, and the like. A particularly preferred embodiment of the oil composition of this disclosure is a lubricating oil formulation.

Preferred oil compositions of this disclosure containing the base stock exhibit a KV100 in a range from kv1 to kv2, where kv1 and kv2 can be 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, as long as kv1<kv2.

Engine oil lubricant grades are determined pursuant to SAE J300 specifications. The low temperature (W) grades (i.e. 10W-xx, 5W-xx, and 0W-xx) are determined by the performance in a combination of viscosity tests including cold crank simulation (CCS) (ASTM D5293) and low-temperature pumping viscosity (ASTM D4684). The high temperature grading for an engine oil (i.e., XW-20, XW-30) is determined by kinematic viscosity at 100° C. (ASTM D445) and high-temp high-shear viscosity (ASTM D4683).

The oil compositions of this disclosure containing the base stock may advantageously exhibit a VI in the range from about 30 to about 200, preferably from about 35 to about 180, more preferably from about 40 to about 150.

The oil compositions of this disclosure containing the base stock advantageously exhibit a NV value of no greater than 20%, preferably no greater than 18%, 16%, 15%, 14%, 12%, 10%, or even 8%.

The oil compositions of this disclosure are particularly advantageous as engine oil for internal combustion engines, including gas engines, diesel engines, natural gas engines, four-stroke engines, two-stroke engines, and rotary engines. The engine oil can be placed into the crank case of the engine to provide the necessary lubrication and cooling effect for the engine during normal operation. The low KV100, coupled with the CCSV of the oil enabled by the use of the base stock makes it particularly fuel efficient. The engine oils are particularly advantageous as passenger vehicle engine oil (PVEO) products.

While it is possible the oil composition of this disclosure contains the base stock as a primary base stock, or even as a single base stock, it is preferable to include the base stock as a co-base stock in combination with one primary base stock and optionally one or more additional co-base stocks. In addition to the base stocks, the oil composition of this disclosure may further comprise additive components.

III.2 Other Base Stocks Useful in the Lubricating Oil

A wide range of lubricating oil base stocks known in the art can be used in conjunction with the base stock in the oil compositions (preferably lubricating oil formulations) of this disclosure, as primary base stock or co-base stock. Such other base stocks can be either derived from natural resources or synthetic, including un-refined, refined, or re-refined oils. Un-refined oil base stocks include shale oil obtained directly from retorting operations, petroleum oil obtained directly from primary distillation, and ester oil obtained directly from a natural source (such as plant matters and animal tissues) or directly from a chemical esterification process. Refined oil base stocks are those un-refined base stocks further subjected to one or more purification steps such as solvent extraction, secondary distillation, acid extraction, base extraction, filtration, and percolation to improve the at least one lubricating oil property. Re-refined oil base stocks are obtained by processes analogous to refined oils but using an oil that has been previously used as a feed stock.

API Groups I, II, III, IV and V are broad categories of base stocks developed and defined by the American Petroleum Institute (API Publication 1509; www.API.org) to create guidelines for lubricant base stocks. Group I base stocks generally have a viscosity index of from about 80 to 120 and contain greater than about 0.03% sulfur and less than about 90% saturates. Group II base stocks generally have a viscosity index of from about 80 to 120, and contain less than or equal to about 0.03% sulfur and greater than or equal to about 90% saturates. Group III base stocks generally have a viscosity index greater than about 120 and contains less than or equal to about 0.03% sulfur and greater than about 90% saturates. Group IV includes polyalphaolefins (PAO). Group V base stocks include base stocks not included in Groups I-IV. The table below summarizes properties of each of these five groups.

disclosure. Natural oils vary also as to the method used for their production and purification, e.g., their distillation range and whether they are straight run or cracked, hydrorefined, or solvent extracted.

Group II and/or Group III base stocks are generally hydroprocessed or hydrocracked base stocks derived from crude oil refining processes.

Synthetic base stocks include polymerized and interpolymerized olefins (e.g., polybutylenes, polypropylenes, propylene isobutylene copolymers, ethylene-olefin copolymers, and ethylene-alphaolefin copolymers).

Synthetic polyalphaolefins ("PAO") base stocks are placed into Group IV. Commercially available Group IV base stocks different from the base stocks of this disclosure, such as those made from one or more of C6, C8, C10, and C12 linear alpha-olefins ("LAO"s) can be advantageously used as a primary or a co-base stock with the base stock of this disclosure. These base stocks can be commercially available at a wide range of viscosity, such as a KV100 in the range from 1.0 to 1,000 cSt. The PAO base stocks can be made by polymerization of the LAO(s) in the presence of Lewis-acid type catalyst, in the presence of a metallocene compound-based catalyst system. High quality Group IV PAO commercial base stocks including the SpectraSyn™ and SpectraSyn Elite™ series available from ExxonMobil Chemical Company having an address at 4500 Bayway Drive, Baytown, Tex. 77450, United States.

All other synthetic base stocks, including but not limited to alkyl aromatics and synthetic esters are in Group V.

Esters in a minor amount may be useful in the lubricating oil formulations of this disclosure. Additive solvency and seal compatibility characteristics may be imparted by the use of esters such as the esters of dibasic acids with monoalkanols and the polyol esters of monocarboxylic acids. Esters of the former type include, e.g., the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc. Useful ester-type Group V base stock include the Esterex™ series commercially available from ExxonMobil Chemical Company.

One or more of the following may be used as a base stock in the oil composition of this disclosure as well: (1) one or

| Base Stock Properties | | | |
|---|---|---|---|
| | Saturates | Sulfur | Viscosity Index |
| Group I | Higher than 90 and/or | Higher than 0.03% and | At least 80 and at most 120 |
| Group II | Higher than 90 and | At most 0.03% and | At least 80 and at most 120 |
| Group III | At least 90 and | At most 0.03% and | At least 120 |
| Group IV | PAO products | | |
| Group V | All other products not included in Groups I, II, III, and IV | | |

Natural oils include animal oils (e.g., lard), vegetable oils (e.g., castor oil), and mineral oils. Animal and vegetable oils possessing favorable thermal oxidative stability can be used. Of the natural oils, mineral oils are preferred. Mineral oils vary widely as to their crude source, e.g., as to whether they are paraffinic, naphthenic, or mixed paraffinic-naphthenic. Oils derived from coal or shale are also useful in this more Gas-to-Liquids (GTL) materials; and (2) hydrodewaxed, hydroisomerized, solvent dewaxed, or catalytically dewaxed base stocks derived from synthetic wax, natural wax, waxy feeds, slack waxes, gas oils, waxy fuels, hydrocracker bottoms, waxy raffinate, hydrocrackate, thermal crackates, foots oil, and waxy materials derived from coal liquefaction or shale oil. Such waxy feeds can be derived from mineral oils or non-mineral oil processing or can be synthetic (e.g., Fischer-Tropsch feed stocks). Such base stocks preferably comprise linear or branched hydrocarbyl compounds of C20 or higher, more preferably C30 or higher.

The oil compositions (preferably lubricating oil formulations) of this disclosure can comprise one or more Group I, II, III, IV, or V base stocks in addition to a base stock of this disclosure. Preferably, Group I base stocks, if any, are present at a relatively low concentration if a high quality lubricating oil is desired. Group I base stocks may be introduced as a diluent of an additive package at a small quantity. Groups II and III base stocks can be included in the lubricating oil formulations of this disclosure, but preferably only those with high quality, e.g., those having a VI from 100 to 120. Group IV and V base stocks, preferably those of high quality, are desirably included into the lubricating oil formulations of this disclosure.

III.3 Lubricating Oil Additives

The oil composition (preferably lubricating oil formulations) of this disclosure may additionally contain one or more of the commonly used lubricating oil performance additives including but not limited to dispersants, detergents, viscosity modifiers, antiwear additives, corrosion inhibitors, rust inhibitors, metal deactivators, extreme pressure additives, anti-seizure agents, wax modifiers, viscosity modifiers, fluid-loss additives, seal compatibility agents, lubricity agents, anti-staining agents, chromophoric agents, defoamants, demulsifiers, densifiers, wetting agents, gelling agents, tackiness agents, colorants, and others. For a review of many commonly used additives and the quantities used, see: (i) Klamann in Lubricants and Related Products, Verlag Chemie, Deerfield Beach, Fla.; ISBN 0-89573-177-0; (ii) "Lubricant Additives," M. W. Ranney, published by Noyes Data Corporation of Parkridge, N J (1973); (iii) "Synthetics, Mineral Oils, and Bio-Based Lubricants," Edited by L. R. Rudnick, C R C Taylor and Francis, 2006, ISBN 1-57444-723-8; (iv) "Lubrication Fundamentals", J. G. Wills, Marcel Dekker Inc., (New York, 1980); (v) Synthetic Lubricants and High-Performance Functional Fluids, 2nd Ed., Rudnick and Shubkin, Marcel Dekker Inc., (New York, 1999); and (vi) "Polyalphaolefins," L. R. Rudnick, Chemical Industries (Boca Raton, Fla., United States) (2006), 111 (Synthetics, Mineral Oils, and Bio-Based Lubricants), 3-36. Reference is also made to: (a) U.S. Pat. No. 7,704,930 B2; (b) U.S. Pat. No. 9,458,403 B2, Column 18, line 46 to Colum 39, line 68; (c) U.S. Pat. No. 9,422,497 B2, Column 34, line 4 to Colum 40, line 55; and (d) U.S. Pat. No. 8,048,833 B2, Column 17, line 48 to Colum 27, line 12, the disclosures of which are incorporated herein in its entirety. These additives are commonly delivered with varying amounts of diluent oil that may range from 5 wt % to 50 wt % based on the total weight of the additive package before incorporation into the formulated oil. The additives useful in this disclosure do not have to be soluble in the lubricating oil formulations. Insoluble additives in oil can be dispersed in the lubricating oil formulations of this disclosure.

When oil compositions (preferably lubricating oil formulations) contain one or more of the additives discussed above, the additive(s) are blended into the oil composition in an amount sufficient for it to perform its intended function.

It is noted that many of the additives are shipped from the additive manufacturer as a concentrate, containing one or more additives together, with a certain amount of base oil diluents.

Examples of techniques that can be employed to characterize the base stock described above include, but are not limited to, analytical gas chromatography, nuclear magnetic resonance, thermogravimetric analysis (TGA), inductively coupled plasma mass spectrometry, differential scanning calorimetry (DSC), and volatility and viscosity measurements.

This disclosure is further illustrated by the following non-limiting examples.

EXAMPLES

In all Examples herein, unless specified otherwise, the following properties are determined pursuant to the following ASTM standards:

| Properties | KV100 | KV40 | VI | Noack Volatility | Pour Point | CCSV |
|---|---|---|---|---|---|---|
| ASTM Standard | D445 | D445 | D2270 | D5800 | D5950 | D5293 |

PART A BASE STOCK EXAMPLES

Example A-1 (Inventive)

A Base Stock Made from 1-Tetradecene Monomer

About 294 grams/hour of a C14 mono-olefin monomer feed (comprising at least 98 wt % of C14 mono-olefin(s) and at least 93.4 wt % of 1-tetradecene) was charged into two continuously-stirred tank reactor ("CSTR") reactors in series. A catalyst promoter system, comprising ethanol and ethyl acetate at approximately 1:1 molar ratio and saturated with $BF_3$, was co-fed with the monomer feed to the upstream CSTR at about 23.4 grams/hour. The reactors were maintained at about 50° C. and continuously pressurized with $BF_3$ gas at a gauge pressure of about 40 kilopascal. Residence time was about 2.03 hours in the upstream reactor and about 1.01 hours in the downstream reactor.

The reaction in the effluent from the downstream reactor was stopped by adding about 1 to 2 grams/hour of a mixture of ethanol and ethyl acetate at about 1:1 molar ratio but free of $BF_3$. The mixture was then neutralized using an excess of 14 wt % NaOH solution. The mixture was allowed to settle. The aqueous layer comprising NaOH and boron-containing salts was disposed. The non-polar layer was recovered and distilled at a temperature in the range from about 124 to 145° C. and a pressure in the range from about 667 Pascal to about 133 Pascal to remove residual monomer (about 52 wt % of the non-polar layer). The oligomer residual from the distillation was subsequently hydrogenated in a batch slurry reactor at about 232° C. and a hydrogen gauge pressure of about 2,410 kilopascal in the presence of a powered nickel catalyst. The hydrogenation was stopped once a sample of the reaction mixture is confirmed to be fully saturated by NMR. The catalyst was filtered out using about 30-78 grams of Celite 545.

Characterization by gas chromatography indicated the base stock product of this Example A-1 comprises about 87.3 wt % of hydrogenated dimers, about 12.3 wt % of hydrogenated trimers and higher oligomers, and about 0.3 wt % of hydrogenated monomer. The product was characterized by $^{13}C$ NMR and analyzed for average percentage of epsilon carbon atoms, and measured for lubricant properties, which data are included in TABLE 1 below.

The base stock product of this Example A-1 exhibits a low KV100, a high viscosity index, and a very low CCSV at −35° C. of 725 mPa·s, rendering it suitable as a primary base stock or a co-base stock in 0W grade formulated engine lubricants, including low-viscosity 0W-4 and 0W-8 grades.

Example A-2 (Inventive)

A Base Stock Made from a Monomer Mixture Comprising 1-Tetradecene and 1-Hexadecene In this inventive Example A-2, a base stock product was made using a method similar to that described in Example A-1 above, using a monomer mixture of a C14 mono-olefin monomer (comprising at least 98 wt % of C14 mono-olefin(s) and at least 93.4 wt % of 1-olefin(s)) and a C16 mono-olefin monomer (comprising at least 97.5 wt % of C16 mono-olefin(s) and at least 92.2 wt % of 1-olefin(s)) at equivalent molar amounts as the mono-olefin monomer feed supplied to the oligomerization reactor. The same catalyst system comprising $BF_3$ and the ethanol/ethyl acetate promoter at about 1:1 molar ratio was used. The residual monomers were distilled at a temperature in the range from 150 to 180° C. and a pressure of about a pressure in the range from about 667 Pascal to about 133 Pascal.

Characterization by gas chromatography indicated the base stock product of this Example A-2 comprises about 93.1 wt % of hydrogenated dimers (including C28, C30, and C32 dimers), and about 6.9 wt % of trimers (including C42, C44, C46, and C48 trimers) and higher oligomers. The base stock was measured for lubricant properties, which data are included in TABLE 1 below.

Example A-3 (Inventive)

A Base Stock Made from 1-Hexadecene

In this inventive Example A-3, a base stock product was made using a method similar to that described in Example A-1 above, using C16 mono-olefin monomer (comprising at least 97.5 wt % of C16 mono-olefin(s) and at least 92.2 wt % of 1-olefin(s)) as the monomer feed supplied to the oligomerization reactor. The same catalyst system comprising $BF_3$ and the ethanol/ethyl acetate promoter at about 1:1 molar ratio was used. The residual monomer was distilled at a temperature in the range from 158 to 185° C. and a pressure of about a pressure in the range from about 1066 Pascal to about 133 Pascal.

Characterization by gas chromatography indicated the base stock product of this Example A-3 comprises about 88.6 wt % of dimers, and about 11.4 wt % of trimers and higher oligomers. The base stock was characterized by $^{13}C$ NMR and analyzed for average percentage of epsilon carbon atoms, and measured for lubricant properties, which data are included in TABLE 1 below.

Example A-C1 (Comparative)

A Base Stock Made from 1-Octadecene

In this comparative Example A-C1, a base stock product was made using a method similar to that described in Example A-1 above, using a C18 mono-olefin feed consisting essentially of 1-hexadecene dissolved in an inert solvent (Sasol C1012 n-paraffin available from Sasol Chemicals North America LLC) with a concentration of the inert solvent of about 10 wt % as the monomer feed supplied to the oligomerization reactor. The same catalyst system comprising $BF_3$ and the ethanol/ethyl acetate promoter at about 1:1 molar ratio was used. The inert solvent was removed by distillation along with the residual monomer at a temperature in the range from about 133 to 187° C. and at a pressure in the range from about 399 to about 133 Pascal.

Characterization by gas chromatography indicated the base stock product of this comparative Example A-C1 comprises about 85.7 wt % of dimers, and about 13.1 wt % of trimers and higher oligomers. The base stock was measured for lubricant properties, which are included in TABLE 1 below.

Example A-C2 (Comparative)

A PAO Base Stock Made from 1-Decene

A PAO base stock having a KV100 of about 3.6 cSt made from substantially pure 1-decene using a catalyst system comprising $BF_3$ and butanol/butyl acetate is used as this comparative Example A-C2 in this disclosure.

Characterization by gas chromatography indicated the base stock product of this comparative Example A-C2 comprises about 95 wt % of trimers, and about 5 wt % of tetramers and higher oligomers. The base stock was characterized by $^{13}C$ NMR and analyzed for average percentage of epsilon carbon atoms, and measured for lubricant properties, which data are included in TABLE 1 below.

Example A-C3 (Comparative)

A PAO Base Stock Made from a Monomer Mixture of 1-Octene, 1-Decene, and 1-Dodecene A PAO base stock having a KV100 of about 4.1 cSt made from a monomer mixture consisting substantially of 1-octene, 1-decene, and 1-dodecene using a catalyst system comprising $BF_3$ and butanol/butyl acetate is used as this comparative Example A-C3 in this disclosure.

Characterization by gas chromatography indicated the base stock product of this comparative Example A-C3 comprises about 72 wt % of trimers of the monomers, and about 28 wt % of tetramers and higher oligomers of the monomers. The base stock was characterized by $^{13}C$ NMR and analyzed for average percentage of epsilon carbon atoms, and measured for lubricant properties, which data are included in TABLE 1 below.

Example A-C4 (Comparative)

A PAO Base Stock Made from a Monomer Mixture Consisting Essentially of 1-Decene and 1-Dodecene A PAO base stock having a KV100 of about 5.1 cSt made from a monomer mixture consisting essentially of 1-decene and 1-dodecene using a catalyst system comprising $BF_3$ and butanol/butyl acetate is used as this comparative Example A-C4 in this disclosure.

Characterization by gas chromatography indicated the base stock product of this comparative Example A-C4 comprises about 69 wt % of trimers of the monomers, and about 31 wt % of tetramers and higher oligomers of the monomers. The base stock was characterized by $^{13}C$ NMR and analyzed for average percentage of epsilon carbon atoms, and measured for lubricant properties, which data are included in TABLE 1 below.

Example A-C5 (Comparative)

A PAO Base Stock Made from a Monomer Mixture Consisting Essentially of 1-Octene, 1-Decene and 1-Dodecene A PAO base stock having a KV100 of about 5.8 cSt made from a monomer mixture consisting essentially of 1-octene, 1-decene and 1-dodecene using a catalyst system comprising $BF_3$ and butanol/butyl acetate is used as this comparative Example A-C5 in this disclosure.

Characterization by gas chromatography indicated the base stock product of this comparative Example A-C5 comprises about 34 wt % of trimers of the monomers, and about 66 wt % of tetramers and higher oligomers of the monomers. The base stock was measured for lubricant properties, which are included in TABLE 1 below. The data in TABLE 1 are further presented in various charts in FIGS. 1, 2, and 3.

FIG. 1 shows the viscosity indexes of the inventive base stocks of Examples A-1, A-2, A-3, and comparative Examples A-C1, A-C2, A-C3, A-C4, and A-C5, as a function of the KV100 of the base stocks. The upper solid line curve connect Examples A-1, A-2, A-3, and A-C1, which comprise as a majority component dimers of a linear alpha-olefin monomer having at least 14 carbon atoms per monomer molecule. The lower dotted line curve connect comparative Examples A-C2, A-C3, A-C4, and A-C5, which comprise as majority components trimers or higher oligomers of linear alpha-olefin monomer(s) having at most 12 carbon atoms per monomer molecule. As can be clearly seen, the base stocks on the upper curve (including those of inventive Examples A-1, A-2, and A-3) tend to exhibit significantly higher viscosity index at comparable KV100 than the base stocks on the lower curve, clearly demonstrating the advantages of the base stocks of this disclosure compared to those made from linear alpha-olefins with shorter chain length having comparable KV100.

Figure 2:
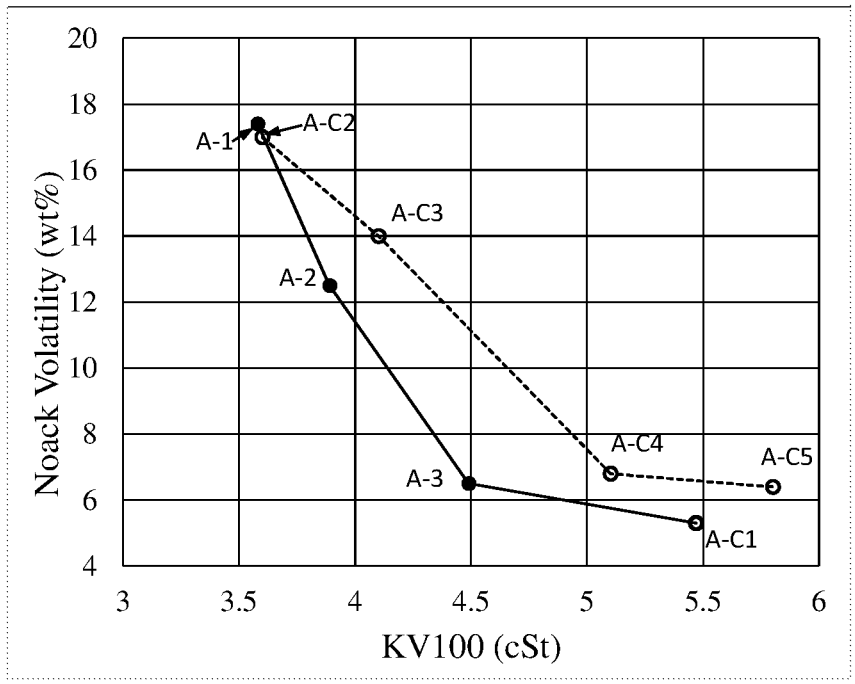
FIG. 2 is a chart showing Noack volatility as a function of kinematic viscosity at 100° C. of the base stocks of the inventive and comparative examples in Part A of the Examples in this disclosure.

FIG. 2 shows the Noack volatility of the base stocks of inventive Examples A-1, A-2, A-3, and comparative Examples A-C1, A-C2, A-C3, A-C4, and A-C5, as a function of the KV100 of the base stocks. The solid line (mostly lower) curve connect Examples A-1, A-2, A-3, and A-C1, which comprise as a majority component dimers of one or more linear alpha-olefin monomer(s) having at least 14 carbon atoms per monomer molecule. The dotted line curve (mostly upper) connect comparative Examples A-C2, A-C3, A-C4, and A-C5, which comprise as majority component trimers or higher oligomers of linear alpha-olefin monomer(s) having at most 12 carbon atoms per monomer molecule. As can be clearly seen, the base stocks on the lower curve (including those of inventive Examples A-1, A-2, and A-3) tend to exhibit comparable or lower Noack volatility at comparable KV100 than the base stocks on the upper curve, clearly demonstrating the advantages of the base stocks of this disclosure compared to those made from linear alpha-olefins with shorter chain length having comparable KV100.

Figure 3:
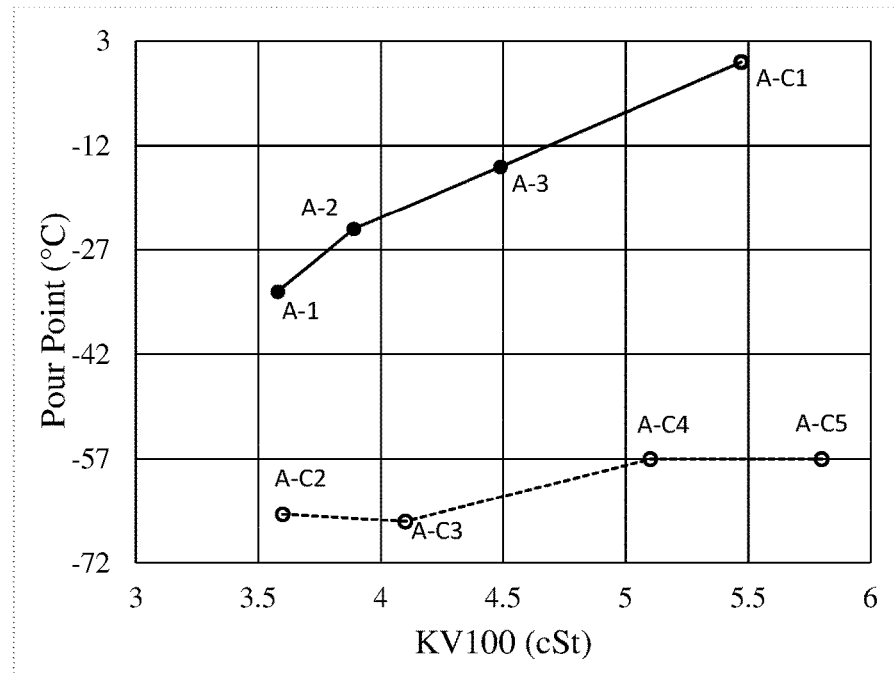
FIG. 3 is a chart showing pour point as a function of kinematic viscosity at 10.c of the base stocks of the inventive and comparative examples in Part A of the Examples in this disclosure.

FIG. 3 shows the pour points of the of the base stocks of inventive Examples A-1, A-2, A-3, and comparative Examples A-C1, A-C2, A-C3, A-C4, and A-C5, as a function of the KV100 of the base stocks. The solid line upper curve connect Examples A-1, A-2, A-3, and A-C1, which comprise as a majority component dimers of a linear alpha-olefin monomer having at least 14 carbon atoms per monomer molecule. The dotted line lower curve connect comparative Examples A-C2, A-C3, A-C4, and A-C5, which comprise as a majority component trimers and/or higher oligomers of linear alpha-olefin monomer(s) having at most 12 carbon atoms per monomer molecule. As can be clearly seen, the base stocks on the upper curve (including those of inventive Examples A-1, A-2, and A-3) tend to exhibit significantly higher pour points at comparable KV100 than the base stocks on the lower curve. Without intending to be bound by a particular theory, it is believed that is because the molecular structures of the base stocks comprising dimers as a majority component are more linear than those of the base stocks comprising timers and/or higher oligomers as majority component, and therefore more waxy. Nonetheless, the base stock of inventive Example A-1 has a low pour point sufficient for a primary base stock in 0W grade engine lubricants as discussed above. Further, as surprisingly demonstrated by the blending examples below, the relatively high pour points of the inventive base stocks do not prevent them from being used as co-base stocks with other Group I, II, III, and IV base stocks to make high-quality formulated engine lubricants, particularly in the 0W grades.

PART B BLENDING EXAMPLES

In this Part B, multiple mixtures of various inventive and comparative base stocks were made and characterized for lubricant properties and performances. Relevant data are reported in TABLEs 2 and 3 below. In TABLEs 2 and 3, the "Treat Rate" of the specific first or second base stock is the concentration by weight of the base stock in the mixture of the first and second base stocks, based on the total weight of the first and second base stocks; "KV100" stands for the measured KV100 of the mixture; "ΔKV100" for the calculated value of {KV100(½)–KV100(2)}, where KV100(½) is the measured KV100 of the mixture, and KV100(2) is the measured KV100 of the PAO-4 second base stock; "% ΔKV100" for the calculated value of {100%*ΔKV100/KV100(2)}; "KV40" for the measured KV40 of the mixture; "VI" for the viscosity index of the mixture; "CCSV" in TABLE 2 for the measured CCSV at –35° C. of the mixture; "ΔCCSV" in TABLE 2 for the calculated value of {CCSV(½)–CCSV(2)}, where CCSV(½) is the measured CCSV at –35° C. of the mixture, and CCSV(2) is the measured CCSV –35° C. of the PAO-4 second base stock; "% ΔCCSV" in TABLE 2 for the calculated value of {100%*ΔCCSV/CCSV (2)}; "Noack Volatility" in TABLE 3 for the measured Noack volatility at 250° C. of the mixture; "Pour Point" in TABLE 3 for the measured pour point of the mixture; and "CCSV @ Temperature" in TABLE 3 for the measured CCSV of the mixture at the various given temperatures.

Example B-1 (Inventive)

In this blending Example B-1, binary mixtures consisting of the base stock product made by the method of Example A-1 as a first base stock and a commercial PAO base stock having a KV100 of 4.147 cSt available from ExxonMobil Chemical Company, having an address at 5200 Bayway Drive, Baytown, Tex. 77520, United States ("PAO-4"), as a second base stock, were formed and measured for lubricant properties.

As can be seen from the data in TABLE 2, blending the base stock of the inventive Example A-1 at a treat rate thereof from 5 to 30 wt % with PAO-4 resulted in mixtures having slightly lower KV100 than the neat PAO-4, and significantly lower CCSV at –35° C., both of which are desirable for engine lubricants. The significant CCSV reduction at –35° C. in the mixtures compared to PAO-4 renders the base stock of inventive Example A-1 particularly advantageous as a co-base stock with PAO-4 in formulating 0W grade engine lubricants.

Example B-2 (Inventive)

In this blending Example B-2, binary mixtures consisting of the base stock made by the method of Example A-2 as a first base stock and the PAO-4 base stock in Example B-1 above (albeit maybe a different batch) as a second base stock were formed and measured for lubricant properties. Data are reported in TABLE 2 below.

As can be seen from the data in TABLE 2, blending the base stock of the inventive Example A-2 at a treat rate thereof from 5 to 30 wt % with PAO-4 resulted in mixtures having slightly lower KV100 than neat PAO-4, which is desirable for engine lubricants. Surprisingly, even though the base stock of inventive Example A-2 has a CCSV at −35° C. of 1559 mPa·s, which is significantly higher than that of the neat PAO-4 (1280 mPa·s), the mixtures demonstrated significantly lower CCSV at −35° C. than the neat PAO-4, which is highly desirable for engine lubricants. The significant CCSV reduction at −35° C. in the mixtures compared to PAO-4 renders the base stock of inventive Example A-2 particularly advantageous as a co-base stock with PAO-4 in formulating 0W grade engine lubricants.

Example B-3 (Inventive)

In this blending Example B-3, binary mixtures consisting of the base stock made by the method of Example A-3 as a first base stock and the PAO-4 base stock in Example B-1 above (albeit maybe a different batch) as a second base stock were formed and measured for lubricant properties. Data are reported in TABLE 2 below.

As can be seen from the data in TABLE 2, blending the base stock of the inventive Example A-3 at a treat rate thereof from 5 to 20 wt % with PAO-4 resulted in mixtures having very similar KV100 to the neat PAO-4, even though the base stock of Example A-3 has a KV100 (4.49 cSt) significantly higher than the neat PAO-4 (4.146 cSt). Surprisingly, even though the base stock of inventive Example A-3 has a CCSV at −35° C. of 733,400 mPa·s, which is significantly higher than that of the neat PAO-4 (1280 mPa·s), the mixtures demonstrated significantly lower CCSV at −35° C. than the neat PAO-4 at a treat rate of the first base stock from 5 to 20 wt %, which is highly desirable for engine lubricants. Even at high treat rates of the first base stock from 30 to 50 wt %, the mixtures had CCSV at −35° C. much lower than the neat base stock of Example A-3. The significant CCSV reduction at −35° C. in the mixtures having treat rates from 5 to 20 wt % of this base stock compared to PAO-4 renders the base stock of inventive Example A-3 particularly advantageous as a co-base stock with PAO-4 in formulating 0W grade engine lubricants.

Example B-C1 (Comparative)

In this blending comparative Example B-C1, binary mixtures consisting of the base stock of comparative Example A-C1 and the PAO-4 base stock in Example B-1 above (albeit maybe a different batch) were formed and measured for lubricant properties. Data are reported in TABLE 2 below.

As can be seen from the data in TABLE 2, blending the base stock of the inventive Example A-C1 at a treat rate thereof from 5 to 50 wt % with PAO-4 resulted in mixtures having higher KV100 and higher CCSV at −35° C. than neat PAO-4.

Example B-C2 (Comparative)

In this blending comparative Example B-C2, binary mixtures consisting of the base stock of comparative Example A-C2 and the PAO-4 base stock in Example B-1 (albeit maybe a different batch) above were formed and measured for lubricant properties. Data are reported in TABLE 2 below.

As can be seen from the data in TABLE 2, blending the base stock of the comparative Example A-C2 at a treat rate thereof from 5 to 30 wt % with PAO-4 resulted in mixtures having slightly lower KV100 than the neat PAO-4, and significantly lower CCSV at −35° C., both of which are desirable for engine lubricants. The significant CCSV reduction at −35° C. in the mixtures compared to PAO-4 renders the base stock of comparative Example A-C2 suitable as a co-base stock with PAO-4 in formulating 0W grade engine lubricants. However, as indicated below, the inventive base stocks of Examples A-1, A-2, and A-3 have advantages over the base stock of comparative Example A-C2 as demonstrated by the charts in FIGS. 4, 5, and 6, which are based on the data in TABLE 2.

Figure 4:
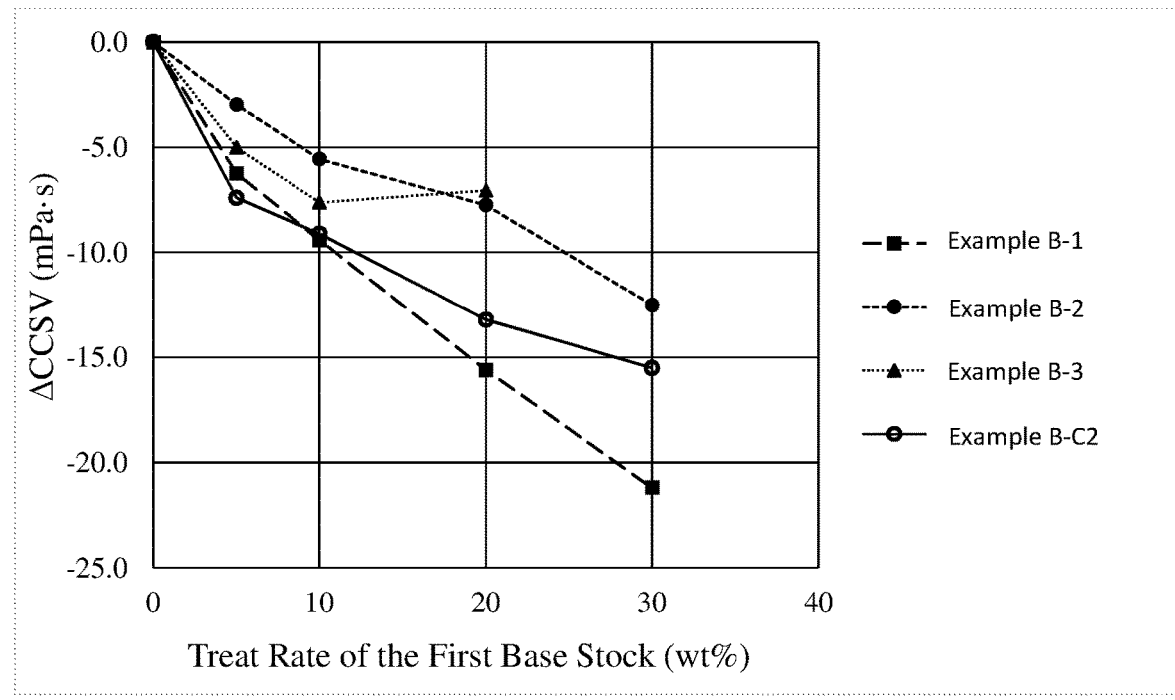
FIG. 4 is a chart showing difference in CCSV at −35° C. of a series of binary mixture oils of an inventive or comparative first base stock and a PAO second base stock relative to the PAO second base stock as a function of the treat rate of the first base stock in the mixture oil, demonstrating the impact on the CCSV at −35° C. of the mixture oil by the inventive or comparative base stock.

FIG. 4 shows ΔCCSV at −35° C. as a function of treat rate of the first base stock in Examples B-1, B-2, B-3, and B-C2. This chart indicates that mixtures formed from inventive base stocks of Example A-1 and comparative base stock of Example A-C2 as the first base stock tend to have similar ΔCCSV (as CCSV reduction compared to neat PAO-4) at treat rates thereof no higher than about 10 wt %. At above 10 wt %, the inventive base stock of Example A-1 tends to cause steeper ΔCCSV (more CCSV reduction compared to neat PAO-4) than the comparative base stock of Example A-C2. At above about 20 wt % of treat rate, the inventive base stock of Example A-2 also tends to cause steeper ΔCCSV (more CCSV reduction relative to neat PAO-4) than the comparable base stock of Example A-C2. Given the significantly higher CCSV at −35° C. of the base stock of Example A-2 (1559 mPa·s) than that of the base stock of Example A-C2 (1080 mPa·s), and that of the PAO-4 (1280 mPa·s), this finding is very surprising and counterintuitive.

Figure 5:
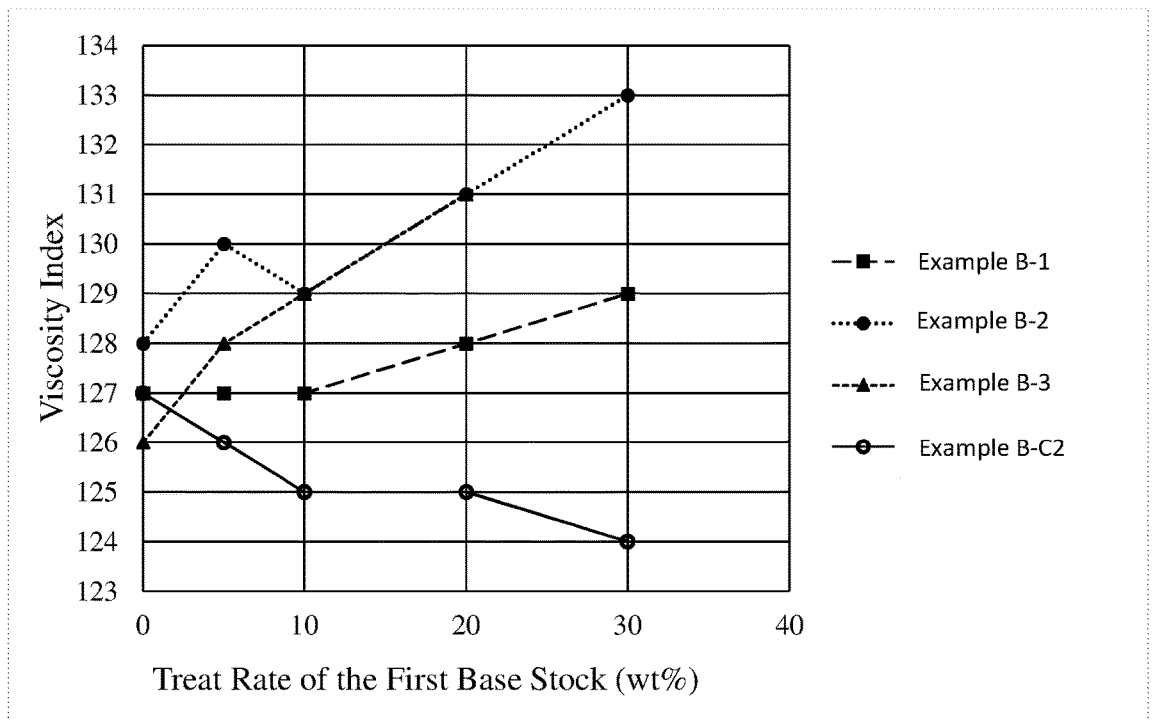
FIG. 5 is a chart showing viscosity index of a series of binary mixture oils of an inventive or comparative first base stock and a PAO second base stock as a function of the treat rate of the first base stock in the mixture oil, demonstrating the impact on the viscosity index of the mixture oil by the inventive or comparative base stock.

FIG. 5 shows viscosity index of the mixture as a function of treat rate of the first base stock in Examples B-1, B-2, B-3, and B-C2. This chart clearly shows that, at treat rates of the first base stock from 5 to 30 wt %, mixtures containing the base stocks of inventive Examples A-1, A-2, A-3, and comparative Example A-C1 as the first base stock, which comprise dimers of linear alpha-olefin(s) as a majority component, exhibited significantly higher viscosity indexes than mixtures containing the base stock of comparative Example A-C2. Indeed, as the treat rate of the first base stock increases, the mixtures comprising the base stocks of inventive Examples A-1, A-2, A-3, and comparative Example A-C1 as the first base stock increase. On the contrary, as the treat rate of the base stock of comparative Example A-C2 increases, the viscosity index of the mixture comprising it as the first base stock decreases.

Example B-4 (Inventive)

In this blending Example B-4, binary mixtures consisting of the base stock of Example A-3 as a first base stock and a commercial Group II base stock, EHC 50, available from ExxonMobil Chemical Company, as a second base stock, were formed and measured for lubricant properties. Data are reported in TABLE 3 below.

Example B-5 (Inventive)

In this blending Example B-5, binary mixtures consisting of the base stock of Example A-3 as a first base stock and a commercial Group III base stock, Yubase 4, available from SK Lubricants Americas Inc. having an address at 11700

Katy Freeway Suite 900, Houston, Tex. 77079, U.S.A., as a second base stock, were formed and measured for lubricant properties. Data are reported in TABLE 3 below.

Example B-6 (Inventive)

In this blending Example B-6, binary mixtures consisting of the base stock of Example A-3 as a first base stock and a commercial Group IV base stock, SpectraSyn™ 6, having a KV100 of about 5.806 cSt and available from ExxonMobil Chemical Company, as a second base stock, were formed and measured for lubricant properties. Data are reported in TABLE 3 below.

Example B-7 (Inventive)

In this blending Example B-7, binary mixtures consisting of the base stock of Example A-3 as a first base stock and a commercial Group IV base stock, SpectraSyn™ 4, having a KV100 of about 4.102 cSt and available from ExxonMobil Chemical Company, as a second base stock, were formed and measured for lubricant properties. Data are reported in TABLE 3 below.

Figure 6:
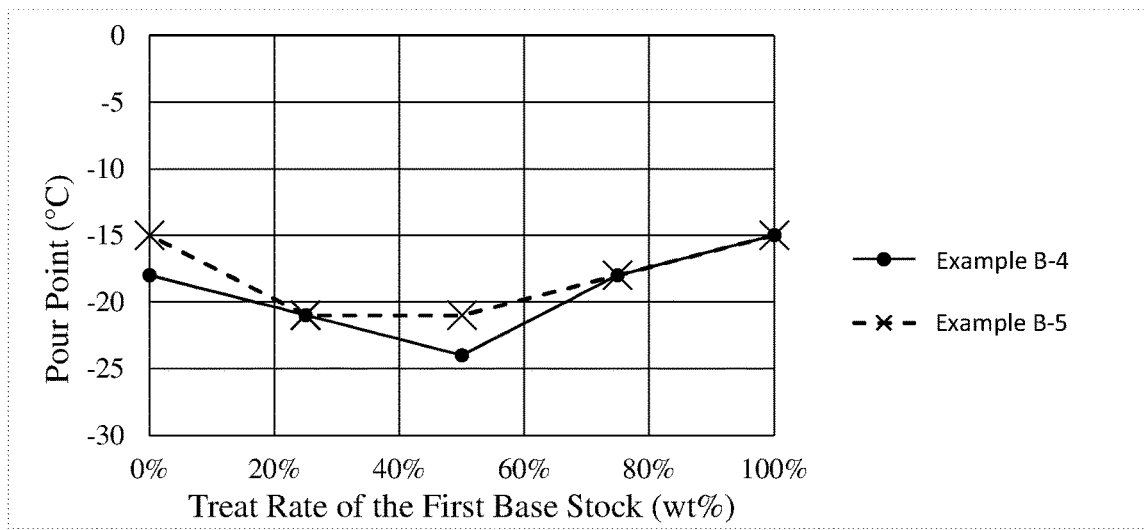
FIG. 6 is a chart showing pour point of a series of binary mixture oils of an inventive base first stock and a Group II or Group III second base stock as a function of the treat rate of the first base stock in the mixture oil, demonstrating the pour point suppressant effect of the inventive base stock when blended with Group II and III base stocks at various treat rate thereof.

FIG. 6 is a chart showing pour point of the mixture as a function of the treat rate of the first base stock (of inventive Example A-3) in Examples B-4 and B-5. Clearly, the base stock of inventive Example A-3 acts as an effective pour point depressant when blended with Groups II and III base stocks at treat rates of the inventive base stock at up to 75 wt %.

Figure 7:
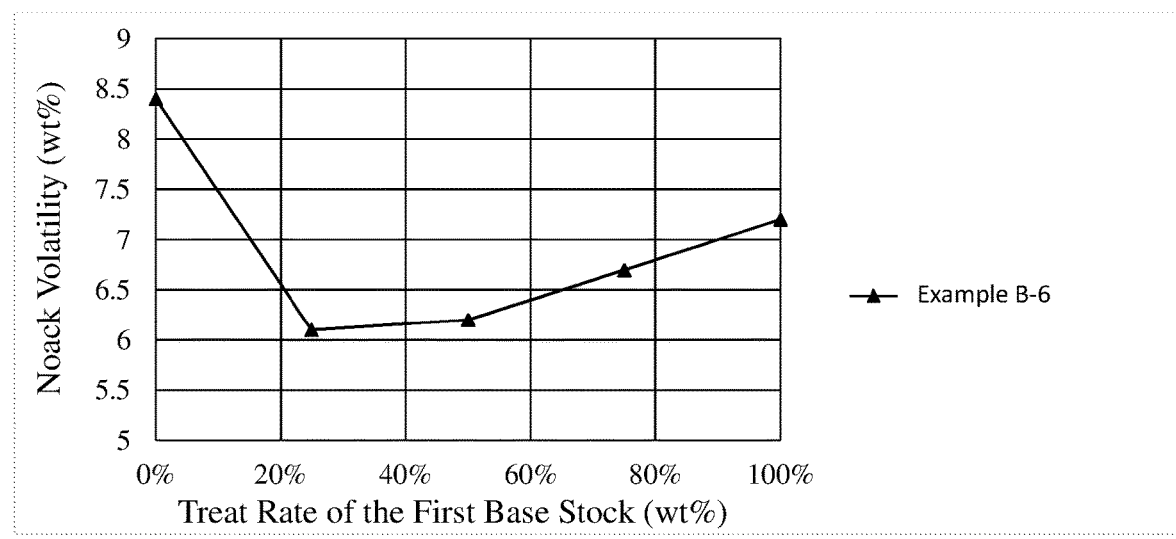
FIG. 7 is a chart showing Noack volatility of a series of binary mixtures of an inventive first base stock and a Group IV second base stock as a function of the treat rate of the first base stock in the mixture oil, demonstrating the Noack volatility suppressant effect of the inventive base stock when blended with the PAO base stock at various treat rate thereof.

FIG. 7 is a chart showing Noack volatility of the mixture as a function of the treat rate of the first base stock (of inventive Example A-3) in Example B-7. Clearly, the base stock of Inventive Example A-3 acts as a Noack volatility depressant when blended with this Group IV base stock at any treat rate.

TABLE 1

| Base Stock of Example No. | | A-1 | A-2 | A-3 | A-C1 | A-C2 | A-C3 | A-C4 | A-C5 |
|---|---|---|---|---|---|---|---|---|---|
| Monomer(s) Used | | C14= | C14=; C16= | C16= | C18= | C10= | C8=; 10=; C12= | C10=; 12= | C8=; C10=; C12= |
| Composition (wt %) | Dimers | 87.3 | 93.1 | 88.6 | 83.5 | — | — | — | — |
| | Trimers and Higher Oligomers | 12.3 | 6.9 | 11.4 | 16.5 | — | — | — | — |
| | Trimers | — | — | — | — | 95 | 72 | 69 | 34 |
| | Tetramers and Higher Oligomers | — | — | — | — | 5 | 28 | 31 | 66 |
| Average percent of epsilon carbon atoms, per molecule (mol %) | | 25.3 | — | 31.1 | — | 15 | 18.7 | 19.4 | — |
| KV100 (cSt) | | 3.58 | 3.89 | 4.49 | 5.47 | 3.6 | 4.1 | 5.1 | 5.8 |
| KV40 (cSt) | | 14.3 | 15.9 | 19.2 | 24.7 | 15.4 | 19.0 | 25.0 | 31.0 |
| Viscosity Index | | 136 | 144 | 153 | 167 | 120 | 126 | 138 | 138 |
| Pour Point (° C.) | | −33 | −24 | −15 | 0 | <−65 | −66 | −57 | −57 |
| Noack Volatility (wt %) | | 17.4 | 12.5 | 6.5 | 5.3 | <17.0 | <14.0 | 6.8 | 6.4 |
| CCSV at −35° C. (mPa · s) | | 725 | 1559 | 733400 | n.d. | 1080 | 1424 | 2420 | n.d. |

C8=: 1-octene; C10=: 1-decene; C12: 1-dodecene; C14=: 1-tetradecene; C16=: 1-hexadecene; C18=: 1-octadecene; CCSV: cold-crank simulator viscosity; n.d.: not determined

TABLE 2

| Example | Of Example | The First Base Stock Treat Rate (wt %) | KV100 (cSt) | ΔKV100 (cSt) | % ΔKV100 (%) | KV40 (cSt) | VI | CCSV (mPa · s) | ΔCCSV (mPa · s) | % ΔCCSV (%) |
|---|---|---|---|---|---|---|---|---|---|---|
| B-1 | A-1 | 0 | 4.147 | 0 | 0 | 18.64 | 127 | 1394 | 0 | 0.0 |
| | | 5 | 4.112 | −0.035 | −0.84 | 18.39 | 127 | 1307 | −87 | −6.2 |
| | | 10 | 4.08 | −0.067 | −1.6 | 18.13 | 127 | 1263 | −131 | −9.4 |
| | | 20 | 4.016 | −0.131 | −3.2 | 17.62 | 128 | 1176 | −218 | −15.6 |
| | | 30 | 3.953 | −0.194 | −4.7 | 17.14 | 129 | 1099 | −295 | −21.2 |
| B-2 | A-2 | 0 | 4.132 | 0 | 0.0 | 18.44 | 128 | 1280 | 0 | 0.0 |
| | | 5 | 4.129 | −0.003 | −0.1 | 18.31 | 130 | 1242 | −38 | −3.0 |
| | | 10 | 4.107 | −0.025 | −0.6 | 18.17 | 129 | 1209 | −71 | −5.5 |
| | | 20 | 4.083 | −0.049 | −1.2 | 17.9 | 131 | 1181 | −99 | −7.7 |
| | | 30 | 4.06 | −0.072 | −1.7 | 17.62 | 133 | 1120 | −160 | −12.5 |
| B-3 | A-3 | 0 | 4.146 | 0 | 0.0 | 18.66 | 126 | 1418 | 0 | 0.0 |
| | | 5 | 4.161 | 0.015 | 0.4 | 18.68 | 128 | 1347 | −71 | −5.0 |
| | | 10 | 4.176 | 0.03 | 0.7 | 18.7 | 129 | 1310 | −108 | −7.6 |
| | | 20 | 4.208 | 0.062 | 1.5 | 18.75 | 131 | 1318 | −100 | −7.1 |
| | | 30 | 4.24 | 0.094 | 2.3 | 18.8 | 134 | 1443 | 25 | 1.8 |
| | | 40 | 4.272 | 0.126 | 3.0 | 18.85 | 136 | 1643 | 225 | 15.9 |
| | | 50 | 4.308 | 0.162 | 3.9 | 18.9 | | 1792 | 374 | 26.4 |
| B-C1 | A-C1 | 0 | 4.154 | 0 | 0.0 | 18.75 | 126 | 1351 | 0 | 0.0 |
| | | 5 | 4.221 | 0.067 | 1.6 | 19.06 | 128 | 1445 | 94 | 7.0 |
| | | 10 | 4.276 | 0.122 | 2.9 | 19.31 | 130 | 1552 | 201 | 14.9 |
| | | 20 | 4.401 | 0.247 | 5.9 | 19.9 | 134 | 1751 | 400 | 29.6 |
| | | 30 | 4.528 | 0.374 | 9.0 | 20.46 | 139 | 2183 | 832 | 61.6 |
| | | 40 | 4.676 | 0.522 | 12.6 | 21.06 | 145 | 3263 | 1912 | 141.5 |
| | | 50 | 4.79 | 0.636 | 15.3 | 21.68 | 148 | 4249 | 2898 | 214.5 |

TABLE 2-continued

The First Base Stock

| Example | Of Example | Treat Rate (wt %) | KV100 (cSt) | ΔKV100 (cSt) | % ΔKV100 (%) | KV40 (cSt) | VI | CCSV (mPa·s) | ΔCCSV (mPa·s) | % ΔCCSV (%) |
|---|---|---|---|---|---|---|---|---|---|---|
| B-C2 | A-C2 | 0 | 4.146 | 0 | 0 | 18.61 | 127 | 1422 | 0 | 0 |
| | | 5 | 4.116 | −0.03 | −0.7 | 18.48 | 126 | 1317 | −105 | −7.4 |
| | | 10 | 4.086 | −0.06 | −1.4 | 18.29 | 125 | 1293 | −129 | −9.1 |
| | | 20 | 4.028 | −0.118 | −2.8 | 17.92 | 125 | 1235 | −187 | −13.2 |
| | | 30 | 3.97 | −0.176 | −4.2 | 17.57 | 124 | 1201 | −221 | −15.5 |

TABLE 3

| Example No. | First Base Stock Treat Rate (wt %) | Second Base Stock Identity | Second Base Stock Treat Rate (wt %) | KV100 (cSt) | KV40 (cSt) | VI | Noack Volitility @ 250° C. (wt %) | Pour Point (° C.) | CCSV @ Temperature (mPa·s) | | | | | |
|---|---|---|---|---|---|---|---|---|---|---|---|---|---|---|
| | | | | | | | | | −10° C. | −15° C. | −20° C. | −25° C. | −30° C. | −35° C. |
| B-4 | 100% | EHC 50 | 0% | 4.461 | 19.01 | 153 | 7.2 | −15 | 19 | 273 | | | | |
| | 75% | | 25% | 4.601 | 20.62 | 144 | 9.3 | −18 | 48 | 314 | | | | |
| | 50% | | 50% | 4.777 | 22.62 | 135 | 10.6 | −24 | 91 | 416 | 622 | | | |
| | 25% | | 75% | 4.982 | 25.21 | 125 | 13.7 | −21 | 195 | 541 | 845 | | | |
| | 0% | | 100% | 5.24 | 28.61 | 115 | 15 | −18 | 373 | 822 | | | | |
| B-5 | 100% | Yubase 4 | 0% | 4.461 | 19.01 | 153 | 7.2 | −15 | 19 | 273 | | | | |
| | 75% | | 25% | 4.401 | 19.04 | 147 | 9.1 | −18 | 12 | 270 | | | | |
| | 50% | | 50% | 4.347 | 19.1 | 140 | 12.1 | −21 | 16 | 294 | 395 | | | |
| | 25% | | 75% | 4.295 | 19.2 | 134 | 14 | −21 | 28 | 309 | 448 | | | |
| | 0% | | 100% | 4.247 | 19.36 | 123 | 14.8 | −15 | 38 | 346 | | | | |
| B-6 | 100% | SpectraSyn™ 6 | 0% | 4.461 | 19.01 | 153 | 7.2 | −15 | 19 | 273 | | | | |
| | 75% | | 25% | 4.738 | 21.09 | 151 | 6.7 | −18 | 65 | 321 | | | | |
| | 50% | | 50% | 5.043 | 23.41 | 149 | 6.2 | −21 | 72 | 378 | 501 | | | |
| | 25% | | 75% | 5.397 | 26.26 | 146 | 6.1 | −30 | 134 | 429 | 625 | 1013 | 1649 | |
| | 0% | | 100% | 5.806 | 29.68 | 142 | 8.4 | −54 | 229 | 560 | 788 | 1287 | 2080 | 3450 |
| B-7 | 100% | SpectraSyn™ 4 | 0% | 4.461 | 19.01 | 153 | 7.2 | −15 | 19 | 273 | | | | |
| | 75% | | 25% | 4.364 | 18.82 | 146 | 9.7 | −18 | −19 | 242 | | | | |
| | 50% | | 50% | 4.275 | 18.65 | 140 | 10.3 | −24 | 3 | 269 | 347 | | | |
| | 25% | | 75% | 4.187 | 18.48 | 133 | 12.5 | −33 | −8 | 262 | 331 | 614 | 924 | |
| | 0% | | 100% | 4.102 | 18.34 | 126 | 12.7 | −75 | −8 | 278 | 337 | 599 | 900 | 1445 |

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

This disclosure has been described above with reference to numerous embodiments and specific examples. Many variations will suggest themselves to those skilled in this art in light of the above detailed description. All such obvious variations are within the full intended scope of the appended claims.

What is claimed is:

1. A base stock comprising: a C28-C32 hydrocarbon fraction ("dimers") produced by oligomerization of an alpha-olefin monomer feed selected from the group consisting of a linear C14 alpha-olefin, a linear C16 alpha-olefin, and a mixture thereof, in the presence of a Lewis acid catalyst system including $BF_3$, ethanol and ethyl acetate, wherein the base stock has,
   a kinematic viscosity at 100° C. as determined pursuant to ASTM D445 ("KV100") of 3.0 cSt to 5.0 cSt,
   a pour point as determined pursuant to ASTM D5850 of −45° C. to −15° C., and
   a cold-crank-simulator viscosity as determined pursuant to ASTM D5293 ("CCSV") at −35° C. of at least 500 mPa·s,
   wherein the total concentration of the dimers is at least 95 wt %, based on the total weight of the base stock.

2. The base stock of claim 1, wherein the dimers have a mole percentage of epsilon-carbons as determined by $^{13}C$ NMR of no less than 20 mol %, based on the total moles of the carbon atoms therein.

3. The base stock of claim 1, wherein the molecules of the dimers comprise, on average, no more than 2.0 branches attached to the carbon backbones therein.

4. The base stock of claim 1, having a cold-crank-simulator viscosity as determined pursuant to ASTM D5293 ("CCSV") at −35° C. of at least 500 mPa·s and less than 1,000 mPa·s.

5. The base stock of claim 1, having a kinematic viscosity at 100° C. as determined pursuant to ASTM D445 ("KV100") in the range from 3.3 to 4.6 cSt.

6. The base stock of claim 1, wherein
   when blended with a PAO reference base stock made from one or more linear alpha-olefin monomer(s) comprising 8 to 12 carbon atoms having a KV100 of 4.0 to 4.2 cSt, a pour point of no higher than −50° C., a CCSV at −35° C. of CCSV(PAO4) mPa·s, where 1200≤CCSV(PAO4)≤1500, to form a first mixture oil comprising 10 wt % of the base stock based on the total weight of the first mixture oil, a second mixture oil comprising 20 wt % of the base stock based on the second mixture oil, and a third mixture oil comprising 30 wt % of the base stock based on the total weight of the base stock, at least one of the following is met:
(i) the first mixture oil exhibits a lower CCSV at −35° C. than the PAO reference base stock;
(ii) the second mixture oil exhibits a lower CCSV at −35° C. than the PAO reference base stock; and
(iii) the third mixture oil exhibits a lower CCSV at −35° C. than the PAO reference base stock.

7. The base stock of claim 6, wherein at least one of the following is met:
(i) the first mixture oil exhibits a CCSV at −35° C. at least 50 mPa·s lower than that of the PAO reference base stock;
(ii) the second mixture oil exhibits a CCSV at −35° C. at least 50 mPa·s lower than that of the PAO reference base stock; and
(iii) the third mixture oil exhibits a CCSV at −35° C. at least 50 mPa·s lower than that of the PAO reference base stock.

8. The base stock of claim 7, wherein the base stock exhibits a CCSV at −35° C. higher than that of the PAO reference base stock.

9. A base stock comprising: a C28 to C32 hydrocarbon first fraction at a concentration of at least 95 wt %, based on the total weight of the base stock and a C42 to C48 second fraction at a concentration in the range from 0 to 5 wt %, based on the total weight of the base stock, wherein the first and second fractions are substantially saturated and produced by oligomerization of an olefin monomer feed selected from the group consisting of a linear C14 alpha-olefin, a linear C16 alpha-olefin, and a mixture thereof,
wherein the base stock includes,
a kinematic viscosity at 100° C. as determined pursuant to ASTM D445 ("KV100") in the range from 3.3 to 4.6 cSt,
a pour point as determined pursuant to ASTM D5850 in the range from −45 to −10° C., and
a cold-crank-simulator viscosity as determined pursuant to ASTM D5293 ("CCSV") at −35° C. of at least 500 mPa·s.

10. An oil composition comprising a base stock of claim 1 as a first base stock, and optionally a Group II, III, or IV base stock different from the first base stock as a second base stock.

11. The oil composition of claim 10 comprising a Group II, III, or IV base stock as the second base stock, wherein the first base stock has a CCSV at −35° C. of CCSV(1), the second base stock has a CCSV at −35° C. of CCSV(2), and the binary mixture of the first base stock and the second base stock in the oil composition absent any component other than the first base stock and the second base stock has a CCSV at −35° C. of CCSV(3), such that:

CCSV(2)>CCSV(3).

12. The oil composition of claim 11, wherein:

(CCSV(2)−CCSV(3))/CCSV(2)≥0.05.

13. The oil composition of claim 12, wherein:
the second base stock comprises a Group II or Group III base stock, and (CCSV(2)−CCSV(3))/CCSV(2)≥0.10.

14. The oil composition of claim 13, wherein:

CCSV(1)≥CCSV(2).

15. A process for making a base stock, the process comprising:
(I) providing an alpha-olefin monomer feed selected from the group consisting of a C14 linear alpha-olefin, a C16 linear alpha-olefin, and a mixture thereof;
(II) contacting the alpha-olefin monomer feed with a catalyst system comprising $BF_3$ in at least one oligomerization reactor under oligomerization conditions to obtain an oligomerization reaction mixture comprising unreacted alpha-olefin monomer(s), dimers, trimers, and the catalyst system;
(III) quenching the oligomerization reaction mixture;
(IV) removing the unreacted monomer(s) from the quenched oligomerization reaction mixture after step (III) to obtain an unsaturated product precursor; and
(V) optionally hydrogenating the unsaturated product precursor in a hydrogenation reactor in the presence of hydrogen under hydrogenation conditions to obtain a hydrogenated oligomer oil; and
(VI) obtaining the base stock comprising dimers and optionally trimers from the unhydrogenated product precursor or hydrogenated dimers and optionally hydrogenated trimers from the hydrogenated oligomer oil, wherein the base stock has,
a kinematic viscosity at 100° C. as determined pursuant to ASTM D445 ("KV100") of 3.0 cSt to 5.0 cSt,
a pour point as determined pursuant to ASTM D5850 of −45° C. to −15° C., and
a cold-crank-simulator viscosity as determined pursuant to ASTM D5293 ("CCSV") at −35° C. of at least 500 mPa·s,
wherein the total concentration of the dimers or the hydrogenated dimers is at least 95 wt %, based on the total weight of the base stock.

16. The process of claim 15, wherein the base stock comprises the trimers at a concentration in the range from 0 to 5 wt %, based on the total weight of the base stock.

17. The process of claim 15, wherein the hydrogenated oligomer oil in step (V) is the base stock without further separation of the dimers from higher oligomers.

18. The process of claim 17, wherein in step (V), the base stock is obtained from the hydrogenated oligomer oil by distillation.

19. The process of claim 18, wherein the total concentration of oligomers comprising at least 56 carbon atoms is no more than 2 wt %, based on the total weight of the base stock.

20. The process of claim 19, wherein in step (II), wherein the catalyst system further comprises ethanol and ethyl acetate in a molar ratio of about 1:1.

21. The process of claim 20, wherein two or more oligomerization reactors connected in series are used in step (II), and the residence time in the downstream reactor is shorter than in the upstream reactor.

* * * * *